United States Patent [19]

Bell et al.

[11] Patent Number: Plant 7,521

[45] Date of Patent: May 14, 1991

[54] MACADAMIA NAMED "HIDDEN VALLEY A16"

[76] Inventors: Henry F. D. Bell; Margaret A. Bell; David J. D. Bell, all of Box 6, Beerwah, Queensland 4519, Australia

[21] Appl. No.: 344,278

[22] Filed: Apr. 26, 1989

[30] Foreign Application Priority Data

Apr. 26, 1988 [AU] Australia ..... 88/002

[51] Int. Cl.[5] ..... A01H 5/00

[52] U.S. Cl. ..... Plt./30

[58] Field of Search ..... Plt./30

*Primary Examiner*—Howard J. Locker

*Attorney, Agent, or Firm*—Quarles & Brady

[57] ABSTRACT

A new variety of macadamia hybrid *integrifolia*×*tetraphylla* has been identified that is particularly characterized by the following combination of characteristics: a low density canopy, a very short flowering period, an elliptical leaf with smooth, lightly undulated and rolled margins, medium pale racemes setting an average of 4.4 nuts per raceme and a nut which is smooth, oval and thin shelled.

3 Drawing Sheets

The present invention is directed to a new and distinct variety of Macadamia tree believed to be a cross of *Macadamia integrifolia*×*tetraphylla* which was identified in a cultivated area.

Among the distinct characterstics of this tree is a combination of: a low density canopy, a very short flowering period, an elliptical leaf which has a smooth, lightly undulated and rolled margin, medium pale racemes, a set of an average of 4.4 nuts per raceme and a nut which is smooth, oval and thin shelled.

Asexual reproduction of the new variety has been accomplished by grafting scion stock taken from the original seedling plant onto both seedling and mature rootstock of various other Macadamia varieties. The variety has maintained character regardless of rootstock, and has exhibited the following characteristics and distinctions true to form through succeeding propagations.

Figure 2:
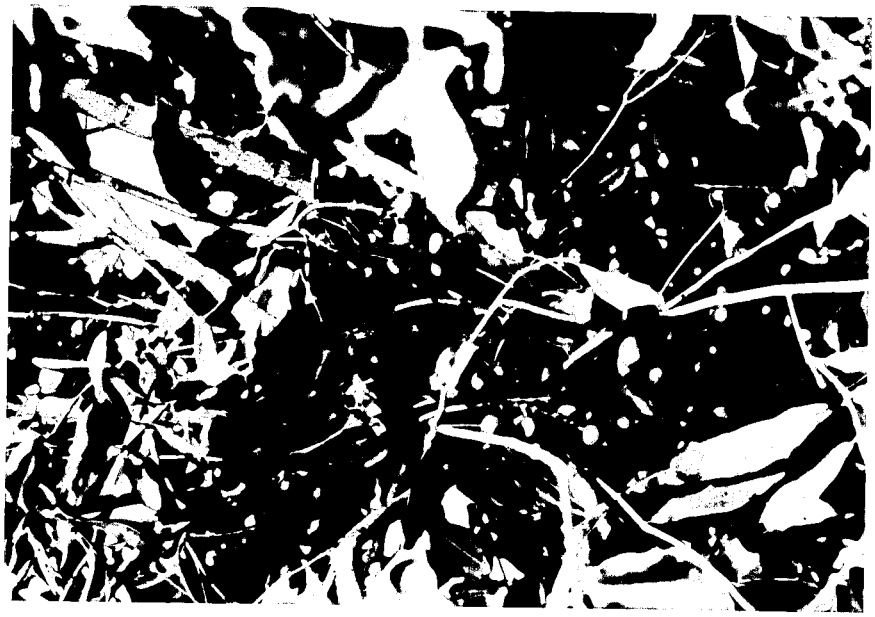
FIG. 2 shows typical nut clusters of the new variety.
Figure 1:
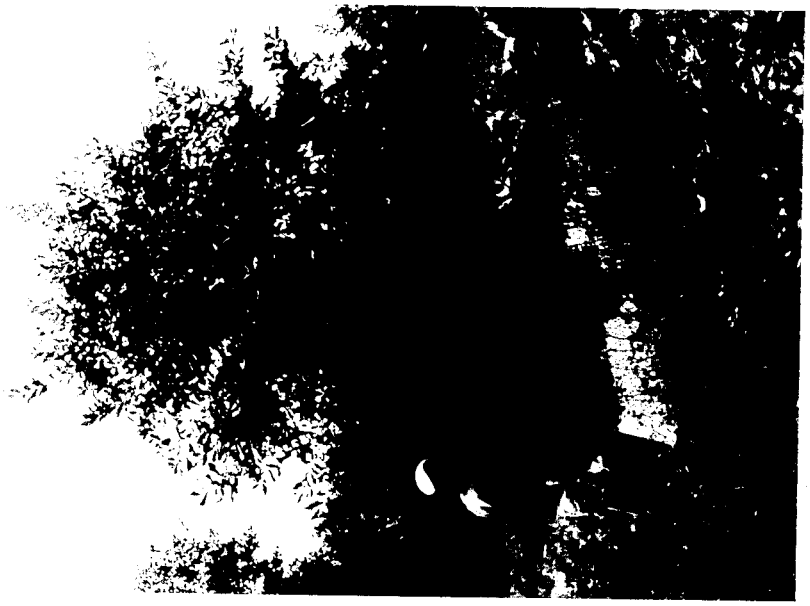
FIG. 1 shows a typical tree specimen of the new variety, named "Hidden Valley A16".
Figure 3:
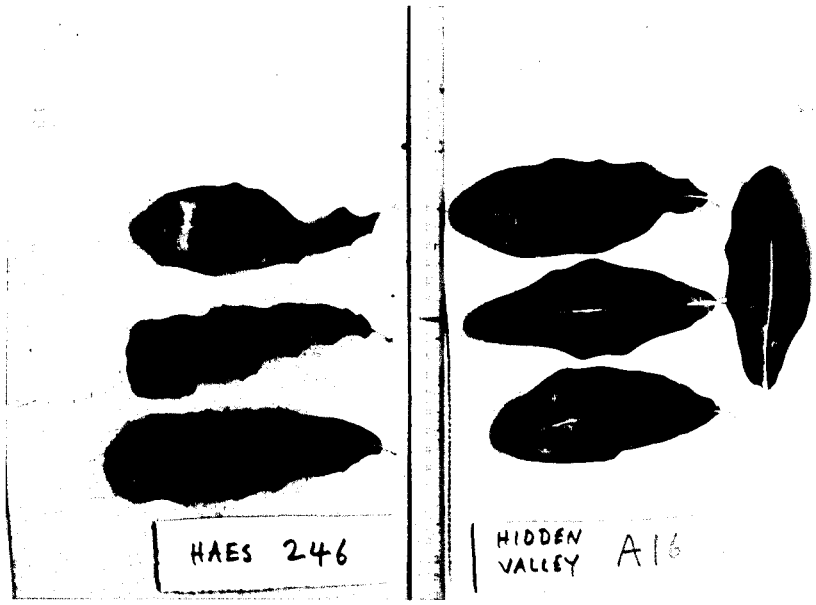
FIG. 3 shows a comparison of the leaves of the new variety with the known variety 'HAES 246'.
Figure 4:
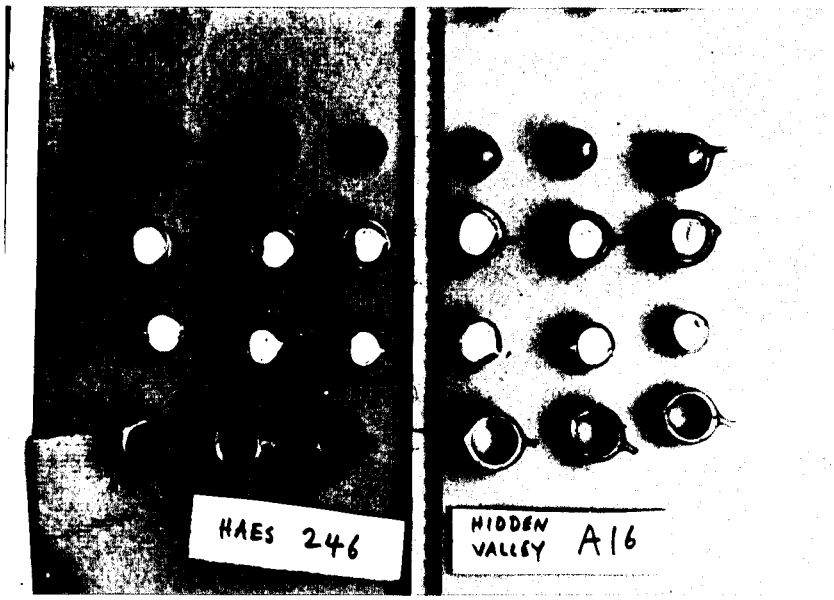
FIG. 4 shows a comparison of the kernel and nut of the new variety with the kernal and nut of the known variety 'HAES 246'.
Figure 5:
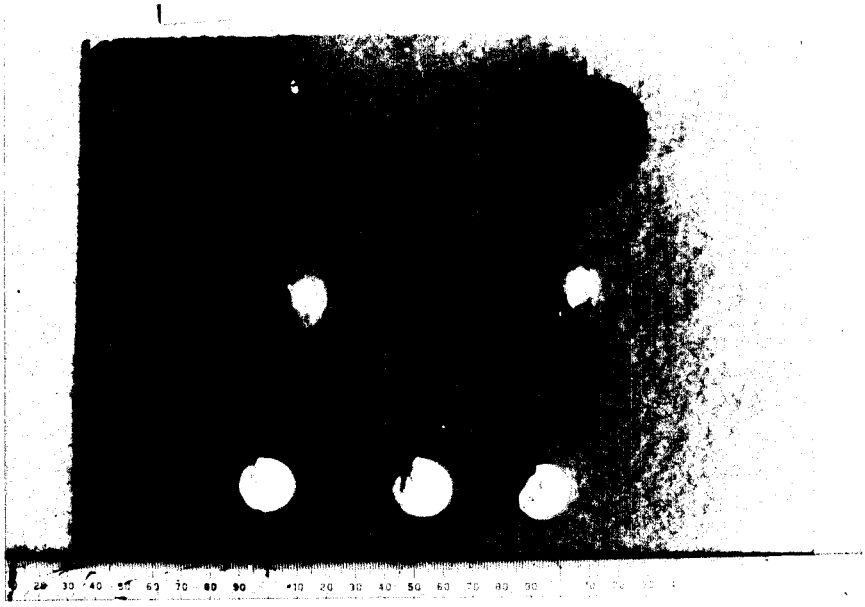
FIG. 5 shows an enlarged view of the kernel and nut of the new variety.

The variety results from a seedling derived from the open pollination of a female parent of the variety Renown, itself a hybrid of *M. integrifolia*×*M. tetraphylla.* The seedling may have arisen from self-pollination or from cross-pollination with the nearest possible pollination parents being of the varieties Own Choice, Keauhou, Kakea and N.R.G. The male parent is believed unlikely to have been self and based on an examination of the morphological character of the plant it is believed that the most likely pollen parent is an *integrifolia* variety such as Kakea or Keauhou. The cultivar has been successfully and successively grafted onto a variety of rootstock yielding trees of consistent character and having good yield characteristics while maintaining current kernel quality and beneficial growth characteristics. The cultivar was discovered and propagated at Hidden Valley Plantations, Beerwah, Queensland, Australia.

The following is a detailed description of the new variety, with color terminology determined in accordance with the Royal Horticultural Society (R.H.S.) Colour Chart number. The characteristics and morphology listed below represent mean measurements from a minimum of one hundred specimens from trees grown in Beerwah, Queensland, Australia.

Tree: The tree is erect in habit (slightly more than Kau), moderately branching with a low density canopy (less than Keauhou or Own Choice). The leaves are arranged predominantly three leaves per node unlike Renown which has predominantly four leaves per node and Hidden Valley A4 which has an even ratio between three- and four-leaf nodes. The grafted material is vigorous in growth (more than Keauhou but less than Hidden Valley A4). The shoots are of medium thickness (thinner than Hidden Valley A4) with an average of 44 mm between nodes, with sparse pubescence and weak anthocyanin coloration (R.H.S. 153A) on the new flush. The tree exhibits an average length juvenile phase (slightly shorter than Keauhou or Kau but longer than Hidden Valley A4).

Leaves: The leaves are elliptical, 2.65 times longer than broad, broader than Own Choice or Keauhou with an obtuse angle rounded tip similar to Kau. The leaf margins are smooth with 0.01 spines per cm and are less undulated than Keauhou. The leaf margins are rolled similar to Own Choice. The young leaves are pale green (R.H.S. 137B), while mature leaves are dark green (R.H.S. 137A), dull surfaced similar to Nutty Glen with distinctly lighter margins (R.H.S. 15D).

*Mean leaf length.*—126.59 mm with standard deviation (s.d.) of 15.29.

*Mean leaf width.*—48.24 mm with s.d. of 5.46.

*Mean petiole length.*—6.8 mm with s.d. of 1.48.

Flower: The racemes are white, medium in length (shorter than Renown) and sparse on the tree compared to Keauhou. The tree has a shorter and lighter flowering period than Keauhou, which starts earlier and finishes later. The flowering observed is mid-season and the length of flowering time is shorter than for any other known variety. The reduced length of flowering time is believed to contribute to an observed light post-anthesis nut drop.

Fruit: The husk is relatively thin (thinner than Renown and similar to Keauhou) with a small hilum end point (about the same as Kau) and an unshouldered pedicel also similar to Kau. Husk dehiscence is partly on the tree (although less so than Nutty Glen or Renown) but is mainly on the ground. There is an average of 4.4 nuts per raceme. There is no pre-germination on the tree observed (as in Nutty Glen) and a very low incidence of fruit remaining on the tree or double-embryo fruit as compared with Own Choice.

*Mean fruit length.*—40.7 mm with s.d. 2.47 (with pedicel and hilum).

*Mean fruit width.*—30.95 mm with s.d. 1.76.

Nut: The nuts are oval, 1.04 times longer than wider, less oval and more even than Renown but less round than Keauhou. The shell is light brown (R.H.S. 164A) with a smooth surface (smoother than Nutty Glen or Renown, but more coarse than Kau) and a moderate sheen (less than Nutty Glen but more than Keauhou). The shell is thinner at the micropyle end (thinner than Keauhou or Kau, but slightly thicker than Nutty Glen). The suture is darker than the shell (R.H.S. 165A), while the micropyle is barely visible. There is no twin mark evident. There is moderate pale flecking (R.H.S. 164C), more than Keauhou but less than Renown or Nutty Glen.

*Mean nut diameter.*—24.97 (Range 19–28 mm) with s.d. 1.27.

*Mean nut weight.*—6.5 gm.

Kernel: The kernel is ovoid, creamy white with very little upper/lower color difference and a mean weight of 2.9 gm. The kernel averages about 45% of the weight of the nut at 1.5% moisture content. 99% of the kernels have an oil accumulation above 72%.

Yield: Recorded nut yields to date have been estimated in trials to be the highest of all tested varieties based on the yield of the original tree. The estimate is based on recording yield per tree divided by tree silhouette area. The original tree's yield estimate is boosted by its relatively small size for its age. The nut yield has grown proportionately faster than the tree. Other trees of the variety are too young, as yet, to assist whether this growth characteristic is characteristic of the variety or simply of the original tree.

The following Table 1 compares many of the features of Hidden Valley A16 (HV A16) with the other varieties Keauhou, Kau, Own Choice, Nutty Glen, and Renown.

| Tree | | | |
|---|---|---|---|
| Character | HV A16 | Keauhou | Kau |
| Growth habit | erect | spreading | erect |
| Canopy density | low | medium | high |
| Lower branch attitude | rising | level | strongly rising |
| Vigour, grafts | strong | medium | med-weak |
| Shoot thickness | med-thin | medium | med-thin |
| Anthocyanin colouration | weak RHS | absent | absent |

-continued

| Tree | | | |
|---|---|---|---|
| Juvenile phase | 152A-B short | medium | long |

| Character | Own Choice | Nutty Glen | Renown |
|---|---|---|---|
| Growth habit | spreading | semi-erect | semi-erect |
| Canopy density | high | low | medium |
| Lower branch attitude | drooping | rising | drooping |
| Vigour, grafts | strong | | strong |
| Shoot thickness | thin | med-thin | medium |
| Anthocyanin colouration | weak | | medium weak |
| Juvenile phase | med-short | | |

| LEAF | | | |
|---|---|---|---|
| Character | HV A16 | Keauhou | Kau |
| No. per axis | 3 | 3 | 3 |
| Shape | Elliptical | Obovate | Obovate |
| Tip | obtuse rounded | obtuse rounded | obtuse pointed |
| Length/breadth | 2.64 | 3.25 | 3.42 |
| length(mm) | 126.59 | 138.82 | 125.09 |
| Petiole length(mm) | 6.78 | 10.43 | 9.24 |
| Marg:Spines /cm | 0.12 | 0.12 | 0.17 |
| Mid portion Undulation | medium | med-strong | med-weak |
| Rolling | medium | med-weak | med-weak |
| Mature colour | dark green | dark green | dark green |
| RHS Chart No. | 137A | 139A | 139A |
| Immature colour | green | green | green |
| RHS Chart No. | 137B | 137A-B | 141A |
| Margin colour | paler | paler | similar |
| Leaf sheen | low | med-high | med-high |
| Vein colour | 153A | 152D | 152C |

| Character | Own Choice | Nutty Glen | Renown |
|---|---|---|---|
| No. per axis | 3 | 4 | 4 |
| Shape | Narrow Elliptical | Narrow Obovate | Broad Lanceolate |
| Tip | obtuse rounded | acute either | acute pointed |
| Length/breadth | 2.81 | 4.53 | 3.91 |
| lenght(mm) | 128.16 | 153.40 | 169.93 |
| Petiole length(mm) | 8.65 | 4.77 | 7.33 |
| Marg:Spines /cm | 0.09 | 0.90 | 0.78 |
| Mid portion Undulation | medium | weak | weak |
| Rolling | med strong | weak | med-weak |
| Mature colour | dark green | dark green | dark green |
| RHS Chart No. | 139A | | 137A |
| Immature colour | green | green | green |
| RHS Chart No. | 137B | | 143A |
| Margin | paler | paler | paler |

-continued

| LEAF | | | |
|---|---|---|---|
| colour | | | |
| Leaf sheen | low | medium | low-med |
| Vein colour | 152D | | 153D |

| FLOWERING AND FRUIT | | | |
|---|---|---|---|
| Character | HV A16 | Keauhou | Kau |
| Flowering time | med-late | medium | v-early |
| Duration | very short | medium | long |
| Nuts/raceme | 4.4 | 1.5(est) | 2.5(est) |
| Raceme density on tree | very light | dense | medium |
| Raceme length | medium | short | short-med |
| Husk color | 137A | 137A | 137B |
| Husk thickness | 3 mm | 3 mm | 2.7 mm |
| % nut diameter | 12% | 11.7% | 10.6% |
| Hilum endpoint | medium-small | medium | small |
| Pedicel shoulder | absent | absent | |
| Dehiscence (1-5) | off-tree 1 | off-tree 1 | off-tree 1 |
| Splitting (1-5) | off-tree 4 | off-tree 5 | off-tree 5 |

| Character | Own Choice | Nutty Glen | Renown |
|---|---|---|---|
| Flowering time | early | late | med-late |
| Duration | | | |
| Nuts/raceme | 2.0(est) | | 1.5(est) |
| Raceme density on tree | dense | | med-dense |
| Raceme length | medium | long | long |
| Husk color | 137A | | 138A |
| Husk thickness | 3.2 mm | 4.3 mm | 4.4 mm |
| % nut diameter | 12.1% | 15.4% | 16.4% |
| Hilum endpoint | med-small | small | large |
| Pedicel shoulder | absent | absent | weak |
| Dehiscence (1-5) | both 2 | | on-tree 3 |
| Splitting | off-tree 4 | on-tree 1 | on-tree |

-continued

| FLOWERING AND FRUIT | |
|---|---|
| (1-5) | 2 |

| NUTS | | | |
|---|---|---|---|
| Character | HV A16 | Keauhou | Kau |
| Nut Shape | oval | round | round |
| length/breadth | 1.04 | 0.98 | 0.99 |
| Nut diameter(mm) | 24.97 | 25.55 | 25.00 |
| Range(mm) | 19-28 | 21-30 | 22-28 |
| Std deviation(mm) | 1.27 | 1.46 | 1.37 |
| Kernel weight(mm) | 2.9-3.5 | 2.3-2.7 | 2.2-2.5 |
| % of Nut | 44-47 | 34-38 | 32-34 |
| Shell texture | smooth | mild-rough | smooth |
| Shell sheen | medium | dull | dull |
| Shell flecking | mod-slight | slight | moderate |
| Micropyle | v-slight | obvious | v-slight |
| Shell colour (dried) | 164A | 165B | 165B |
| Suture colour | darker | same | lighter |

| Character | Own Choice | Nutty Glen | Renown |
|---|---|---|---|
| Nut Shape | round | round | oval |
| length/breadth | 1.04 | 0.99 | 1.12 |
| Nut diameter(mm) | 25.96 | 28.04 | 26.85 |
| Range(mm) | 21-30 | 23-34 | 23-30 |
| Std deviation(mm) | 1.57 | 2.02 | 1.45 |
| Kernel weight(mm) | 2.5-2.7 | 4.0 | 3.2-3.6 |
| % of Nut | 33-36 | 46-47 | 39-41 |
| Shell texture | smooth | rough | rough |
| Shell sheen | dull | med-shiny | shiny |
| Shell flecking | mod-heavy | mod-slight | mod-heavy |
| Micropyle | v-slight | v-slight | v-slight |
| Shell colour (dried) | 165A-B | 165A-B | 165B |
| Suture colour | same | same | lighter |

We claim:

1. A new and distinct hybrid *Macadamia integrifolia* × *tetraphylla* named Hidden Valley A16 substantially as shown and described.

* * * * *